United States Patent
Andree et al.

[11] Patent Number: 6,074,989
[45] Date of Patent: Jun. 13, 2000

[54] SUBSTITUTED AZOLYLSULPHONYLPHENYLURACILS

[75] Inventors: Roland Andree; Mark Wilhelm Drewes, both of Langenfeld; Markus Dollinger; Hans-Joachim Santel, both of Leverkusen, all of Germany

[73] Assignee: Bayer Aktiengesellschaft, Leverkusen, Germany

[21] Appl. No.: 08/817,843

[22] PCT Filed: Oct. 23, 1995

[86] PCT No.: PCT/EP95/04146

§ 371 Date: Apr. 25, 1997

§ 102(e) Date: Apr. 25, 1997

[87] PCT Pub. No.: WO96/14315

PCT Pub. Date: May 17, 1997

[30] Foreign Application Priority Data

Nov. 4, 1994 [DE] Germany .............................. 44 39 332

[51] Int. Cl.[7] .......................... C07D 239/54; A01N 43/54
[52] U.S. Cl. ............................. 504/243; 544/310
[58] Field of Search .............. 504/243; 544/310

[56] References Cited

U.S. PATENT DOCUMENTS 5,169,430  12/1992  Strunk ..................................... 544/310

FOREIGN PATENT DOCUMENTS 362606    9/1989   European Pat. Off. .
A 0 362 606  4/1990   European Pat. Off. .
A 25 09 037  9/1976   Germany .

*Primary Examiner*—John M. Ford
*Attorney, Agent, or Firm*—Sprung Kramer Schaefer & Briscoe

[57] ABSTRACT

The invention relates to novel substituted azolylsulphonylphenyluracils of the general formula (I)

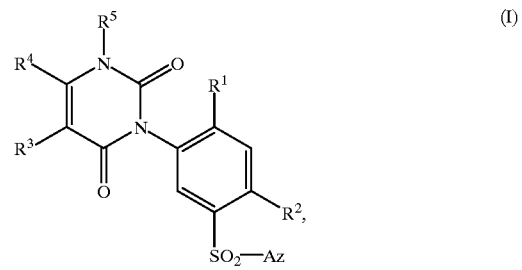

in which
Az represents optionally substituted azolyl,
$R^1$ represents hydrogen, cyano or halogen,
$R^2$ represents cyano, nitro, halogen or a respectively optionally substituted radical of the group consisting of alkyl and alkoxy,
$R^3$ represents hydrogen, halogen, alkyl or halogenoalkyl,
$R^4$ represents hydrogen, alkyl or halogenoalkyl, and
$R^5$ represents hydrogen, amino, formyl or a respectively optionally substituted radical from the group consisting of alkyl, alkenyl or alkinyl,
a process for their preparation and their use as herbicides.

6 Claims, No Drawings

SUBSTITUTED AZOLYLSULPHONYLPHENYLURACILS

This is a 371 of PCT/EP95/04146 filed Oct. 23, 1995.

The invention relates to novel substituted azolylsulphonylphenyluracils, a process for their preparation and their use as herbicides.

Certain heterocyclylsulphonylphenyluracils, such as, for example, the compounds 1-[2-chloro-5-(3,6-dihydro-3-methyl-2,6-dioxo-4-trifluoromethyl-1(2H)-pyridiminyl)-4-fluoro-phenylsulphonyl]-pyrrolidine and 4-[2-chloro-5-(3,6-dihydro-3-methyl-2,6-dioxo-4-trifluoromethyl-1(2H)-pyrimidinyl)-4-fluoro-phenylsulphonyl]-morpholine, are known to have herbicidal properties (cf. U.S. Pat. No. 5,169,430). However, the activity of these compounds is not always entirely satisfactory, in particular at low application rates and active compound concentrations.

This invention, then, provides novel substituted azolylsulphonylphenyluracils of the general formula (I)

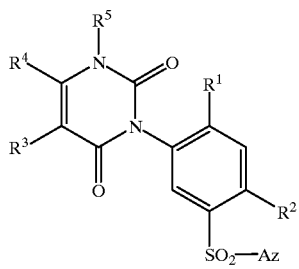

in which

Az represents optionally substituted azolyl,
$R^1$ represents hydrogen, cyano or halogen,
$R^2$ represents cyano, nitro, halogen or a respectively optionally substituted radical of the group consisting of alkyl and alkoxy,
$R^3$ represents hydrogen, halogen, alkyl or halogenoalkyl,
$R^4$ represents hydrogen, alkyl or halogenoalkyl, and
$R^5$ represents hydrogen, amino, formyl or a respectively optionally substituted radical from the group consisting of alkyl, alkenyl or alkinyl.

The novel substituted azolylsulphonylphenyluracils of the general formula (I) are obtained when chlorosulphonylphenyluracils of the general formula (II)

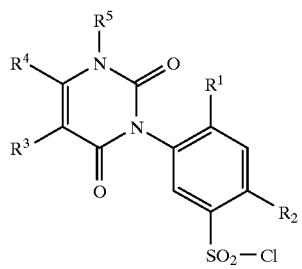

in which $R^1$, $R^2$, $R^3$, $R^4$ and $R^5$ are each as defined above, are reacted with azoles of the general formula (III)

 (III)

in which

Az is as defined above, if appropriate in the presence of a reaction auxiliary and if appropriate in the presence of a diluent.

The novel substituted azolylsulphonylphenyluracils of the general formula (I) have a pronounced and selective herbicidal action.

Preference is given to compounds of the formula (I) in which

Az represents pyrazolyl, imidazolyl or triazolyl, each of which is optionally mono- to trisubstituted by identical or different substituents from the group consisting of halogen, cyano, nitro, amino, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy or halogeno-$C_1$–$C_4$-alkylthio, $R^1$ represents hydrogen, cyano, fluorine or chlorine, $R^2$ represents cyano, nitro, fluorine, chlorine, bromine or a respectively optionally fluorine- and/or chlorine-substituted radical from the group consisting of $C_1$–$C_4$-alkyl and $C_1$–$C_4$-alkoxy, $R^3$ represents hydrogen, fluorine, chlorine, bromine or optionally fluorine- and/or chlorine-substituted $C_1$–$C_4$-alkyl, $R^4$ represents hydrogen or optionally fluorine- and/or chlorine-substituted $C_1$–$C_4$-alkyl, and $R^5$ represents hydrogen, amino, formyl or a respectively optionally cyano-, fluorine- and/or chlorine-, methoxy- or ethoxy-substituted radical from the group consisting of $C_1$–$C_4$-alkyl, $C_1$–$C_4$-alkenyl and $C_1$–$C_4$-alkinyl In the definitions, the saturated or unsaturated hydrocarbon chains, such as alkyl, alkenyl or alkinyl are in each case—even in combination with heteroatoms, such as in alkoxy—straight-chain or branched.

Halogen generally represents fluorine, chlorine, bromine or iodine, preferably fluorine, chlorine or bromine, in particular fluorine or chlorine.

The invention provides in particular compounds of the formula (I) in which

Az represents pyrazolyl or imidazolyl, each of which is optionally mono-, di- or trisubstituted by identical or different substituents from the group consisting of chlorine, bromine, methyl, ethyl or trifluoromethyl, $R^1$ represents hydrogen, fluorine or chlorine, $R^2$ represents cyano or chlorine, $R^3$ represents hydrogen, fluorine, chlorine, bromine or respectively optionally fluorine- and/or chlorine-substituted methyl or ethyl, $R^4$ represents respectively optionally fluorine- and/or chlorine-substituted methyl or ethyl, and $R^5$ represents hydrogen, amino or respectively optionally fluorine- and/or chlorine-substituted methyl, ethyl, n- or i-propyl, propenyl or propinyl The abovementioned general or preferred radical definitions apply both to the end products and to the corresponding precursors or intermediates. These radical definitions can be combined with each other as desired, that is to say combinations between the respective ranges of preferred compounds are also possible.

Examples of compounds of the formula (I) are listed in groups below.

Group 1

(IA-1)

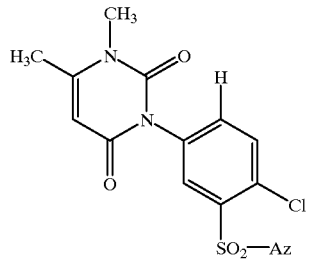

Az has, for example, the meanings listed below: pyrazol-1-yl, imidazol-1-yl, 1,2,4-triazol-1-yl, 1,3,4-triazol-1-yl, 3-methyl-pyrazol-1-yl, 4-methyl-pyrazol-1-yl, 5-methyl-pyrazol-1-yl, 3,5-dimethyl-pyrazol-1-yl, 3,4,5-trimethyl-pyrazol-1-yl, 4-chloro-pyrazol-1-yl, 4-bromo-pyrazol-1-yl, 4-chloro-3-methyl-pyrazol-1-yl, 4-bromo-3-methyl-pyrazol-1-yl, 4-chloro-3,5-dimethyl-pyrazol-1-yl, 4-bromo-3,5-dimethyl-pyrazol-1-yl, 2-methyl-imidazol-1-yl, 4-methyl-imidazol-1-yl, 2,4-dimethyl-imidazol-1-yl and 3,5-dimethyl-1,2,4-triazol-1-yl.

Group 2

(IA-2)

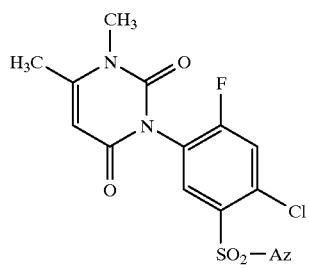

Az has, for example, the meanings listed above for group 1.

Group 3

(IA-3)

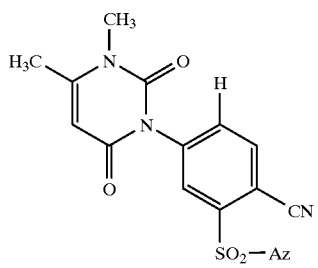

Az has, for example, the meanings listed above for group 1.

Group 4

(IA-4)

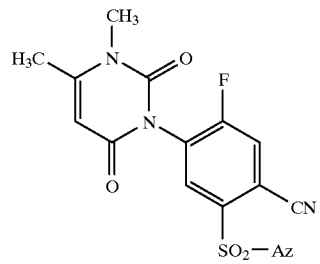

Az has, for example, the meanings listed above for group 1.

Group 5

(IA-5)

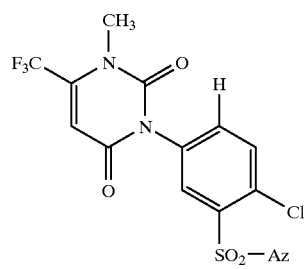

Az has, for example, the meanings listed above for group 1.

Group 6

(IA-6)

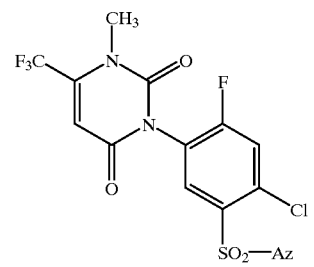

Az has, for example, the meanings listed above for group 1.

Group 7

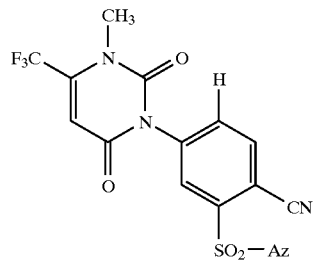
(IA-7)

Az has, for example, the meanings listed above for group 1.

Group 8

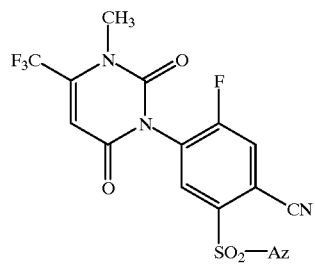

Az has, for example, the meanings listed above for group 1.

Group 9

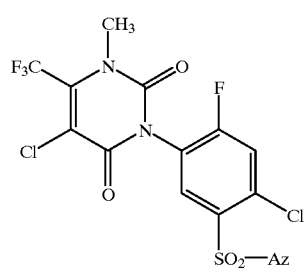
(IA-9)

Az has, for example, the meanings listed above for group 1.

Group 10

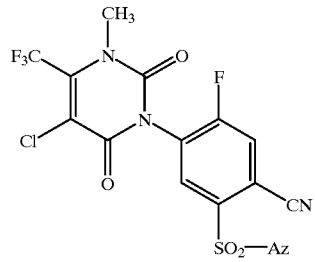
(IA-10)

Az has, for example, the meanings listed above for group 1.

Group 11

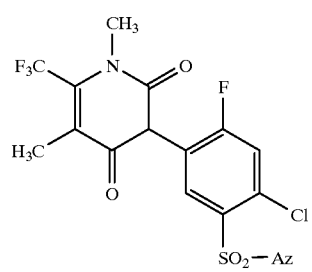
(IA-11)

Az has, for example, the meanings listed above for group 1.

Group 12

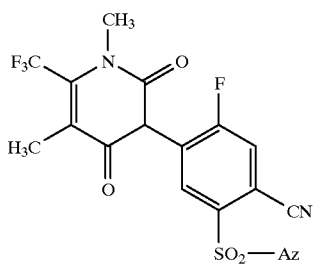
(IA-12)

Az has, for example, the meanings listed above for group 1.

Group 13

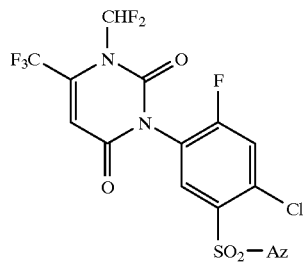
(IA-13)

Az has, for example, the meanings listed above for group 1.

Group 14

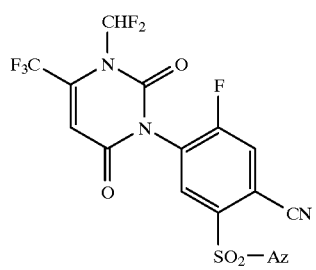
(IA-14)

Az has, for example, the meanings listed above for group 1.

Group 15

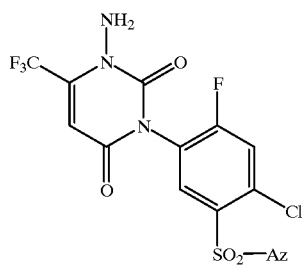
(IA-15)

Az has, for example, the meanings listed above for group 1.

Group 16

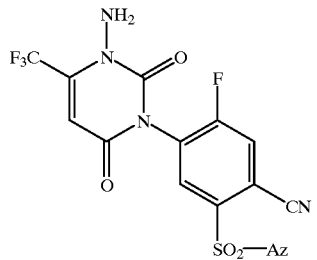
(IA-16)

Az has, for example, the meanings listed above for group 1.

Group 17

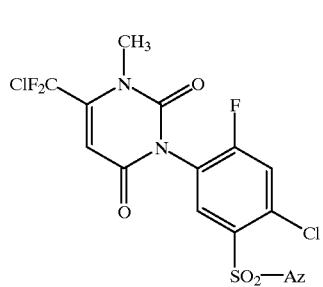
(IA-17)

Az has, for example, the meanings listed above for group 1.

Group 18

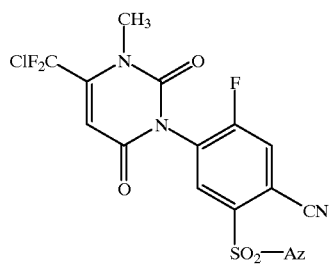
(IA-18)

Az has, for example, the meanings listed above for group 1.

Group 19

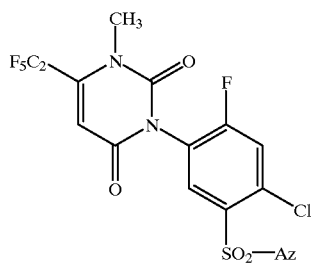
(IA-19)

Az has, for example, the meanings listed above for group 1.

Group 20

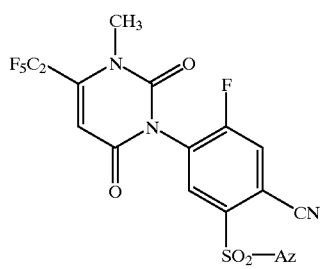
(IA-20)

Az has, for example, the meanings listed above for group 1.

If, for example, 2-chloro-4-fluoro-5-(3,6-dihydro-3-methyl-4-trifluoromethyl-2,6-dioxo-1(2H)-pyrimidinyl)-benzenesulphonyl chloride and imidazole are used as starting materials, the course of the reaction of the process according to the invention can be represented by the following scheme:

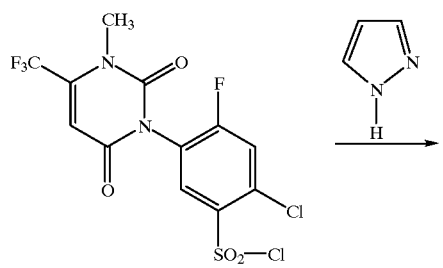

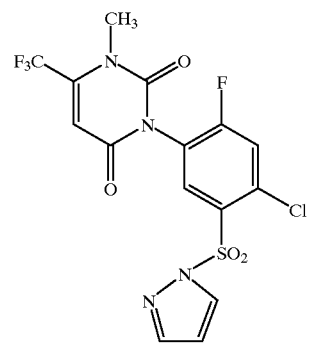

The chlorosulphonylphenyluracils to be used as starting materials in the process according to the invention for preparing the compounds of the general formula (I) are defined in a general way by the formula (II). In the formula (II), $R^1$, $R^2$, $R^3$, $R^4$ and $R^5$ each preferably or in particular have those meanings already given above in connection with the description of the compounds of the formula (I) as preferred or as particularly preferred for $R^1$, $R^2$, $R^3$, $R^4$ and $R^5$.

The starting materials of the formula (II) are known and/or can be prepared by known processes (cf. U.S. Pat. No. 5,169,430).

The azoles further to be used as starting materials in the process according to the invention are defined in a general way by the formula (III). In the formula (III), Az preferably or in particular has the meaning already given above in connection with the description of the compounds of the formula (I) as preferred or as particularly preferred for Az.

The starting materials of the formula (III) are known organic chemicals.

The process according to the invention is preferably carried out in the presence of a suitable reaction auxiliary. Suitable reaction auxiliaries are all customary inorganic or organic bases. These are for example alkali metal or alkaline earth metal hydrides, hydroxides, amides, alcoholates, acetates, carbonates or hydrogencarbonates, such as, for example, lithium hydride, sodium hydride, potassium hydride or calcium hydride, lithium amide, sodium amide or potassium amide, sodium methoxide or potassium methoxide, sodium ethoxide or potassium ethoxide, sodium propoxide or potassium propoxide, aluminium isopropoxide, sodium tert-butoxide or potassium tert-butoxide, sodium hydroxide or potassium hydroxide, ammonium hydroxide, sodium acetate, potassium acetate or calcium acetate, ammonium acetate, sodium carbonate, potassium carbonate or calcium carbonate, ammonium carbonate, sodium hydrogencarbonate or potassium hydrogencarbonate, and also basic organic nitrogen compounds such as trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethyl-benzylamine, pyridine, 2-methyl-, 3-methyl- and 4-methyl-pyridine, 2,4-dimethyl-, 2,6-dimethyl-, 3,4-dimethyl- and 3,5-dimethyl-pyridine, 5-ethyl-2-methyl-pyridine, N-methylpiperidine, N,N-dimethylaminopyridine, diazabicyclooctane (DABCO), diazabicyclononene (DBN) or diazabicycloundecene (DBU).

Suitable diluents for carrying out the process according to the invention are the customary organic solvents. These are in particular aliphatic, alicyclic or aromatic, optionally halogenated hydrocarbons, such as, for example, pentane, hexane, heptane, petroleum ether, ligroin, benzine, benzene, toluene, xylene, chlorobenzene, dichlorobenzene, cyclohexane, methylcyclohexane, dichloromethane, chloroform, carbon tetrachloride; ethers, such as diethyl ether, diisopropyl ether, t-butyl methyl ether, t-pentyl methyl ether, dioxane, tetrahydrofuran, ethylene glycol dimethyl ether, ethylene glycol diethyl ether, or diethylene glycol dimethyl ether or diethylene glycol diethyl ether; ketones, such as acetone, butanone or methyl isobutyl ketone; nitrites, such as acetonitrile, propionitrile, butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate, ethyl acetate, n- or i-propyl acetate, or n-, i- or s-butyl acetate, sulphoxides, such as dimethyl sulphoxide, alcohols, such as methanol, ethanol, n- or i-propanol, n-, i-, s- or t-butanol, ethylene glycol monomethyl ether, ethylene glycol monoethyl ether, diethylene glycol monomethyl ether, diethylene glycol monoethyl ether, their mixtures with water or pure water.

In the practice of the process according to the invention, the reaction temperatures may be varied over a relatively wide range. In general, temperatures of between −10° C. and +100° C., preferably temperatures of between 0° C. and +80° C., in particular temperatures of between 10° C. and 60° C., are employed.

The process according to the invention is generally carried out under atmospheric pressure. However, it is also possible to operate under elevated or reduced pressure—in general between 0.1 bar and 10 bar.

The starting materials required in each case to carry out the process according to the invention are generally employed in approximately equimolar quantities. However, it is also possible to use one of the two components employed in each case in a relatively large excess. The reactions are generally carried out in a suitable diluent, in the presence of an acid acceptor, and the reaction mixture is stirred for several hours at the temperature required in each case. In the process according to the invention, work-up takes place in each case according to customary methods (cf. the Preparation Examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention are suitable in particular for the selective control of monocotyledon and dicotyledon weeds in monocotyledon and dicotyledon crops, both pre- and post-emergence.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic ester such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil; dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuronmethyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds such as fungicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the examples which follow.

PREPARATION EXAMPLES

Example 1

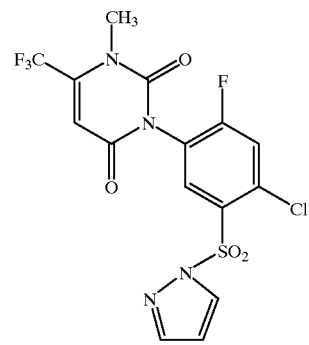

A solution of 1.1 g (2.5 mmol) of 2-chloro-4-fluoro-5-(3, 6-dihydro-3-methyl-4-trifluoromethyl-2,6-dioxo-1(2H)-pyrimidinyl)-benzenesulphonyl chloride in 20 ml of methylene chloride is added dropwise with stirring to a mixture of 0.2 g (2.5 mmol) of pyrazole, 0.2 g of pyridine and 20 ml of methylene chloride, and the reaction mixture is stirred at about 20° C. for 18 hours. The mixture is then washed twice with 0.1 N hydrochloric acid, dried with sodium sulphate and filtered. The solvent is carefully distilled off from the filtrate using a water pump vacuum.

0.7 g (62% of theory) of 1-[2-chloro-4-fluoro-5-(3,6-dihydro-3-methyl-4-trifluoromethyl-2,6-dioxo-1(2H)-pyrimidinyl)-phenylsulphonyl]-pyrazole of melting point 172° C. are obtained.

In addition, by the method of Example 1 and according to the general description of the preparation process according to the invention, for example the compounds of the formula (I) listed in Table 1 below can be prepared.

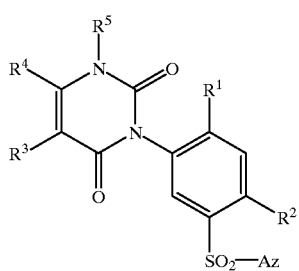

(I)

TABLE 1

Examples of compounds of the formula (I)

| Ex. No. | R¹ | R² | R³ | R⁴ | R⁵ | Az | Physical data |
|---|---|---|---|---|---|---|---|
| 2 | F | Cl | H | CF₃ | CH₃ | 3-CH₃-pyrazolyl | mp.: 154° C. |
| 3 | F | Cl | H | CF₃ | CH₃ | 4-CH₃-pyrazolyl | mp.: 70° C. |
| 4 | F | Cl | H | CF₃ | CH₃ | 3,5-(CH₃)₂-pyrazolyl | mp.: 67° C. |
| 5 | F | Cl | H | CF₃ | CH₃ | 4-Br-3,5-(CH₃)₂-pyrazolyl | mp.: 75° C. |
| 6 | F | Cl | H | CF₃ | CH₃ | 4-Br-3-CH₃-pyrazolyl | mp.: 175° C. |
| 7 | F | Cl | H | CF₃ | H | 4-Br-3,5-(CH₃)₂-pyrazolyl | mp.: 235° C. |
| 8 | F | Cl | H | CF₃ | H | 4-Br-3-CH₃-pyrazolyl | ¹H-NMR (DMSO-D₆, d): 6.47 ppm |
| 9 | F | Cl | H | CF₃ | CH₃ | 4-Cl-3,5-(CH₃)₂-pyrazolyl | mp.: 141° C. |

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance. Only the amount of active compound applied per unit area being decisive. After three weeks, the degree of damage to the plants is rated in % damage in comparison to the development of the untreated control.

The figures denote:

0%=no action (like untreated control)

100%=total destruction

In this test, for example the compounds obtained by preparation examples 1 and 2 are well tolerated by crops, such as, for example, barley (10%), and exhibit strong activity against weeds, such as, for example, digitaria (95–100%), panicum (100%), chenopodium (100%) and polygonum (100%).

Example B

Pre-emergence test/outdoor

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Shortly after sowing the seeds of the test plants in the field, the individual plots were watered with the amount of active compound preparation necessary for wetting the soil surface evenly. The concentration of the active compound in the preparation is of no importance, only the amount of active compound applied per unit area being decisive.

After 5 weeks, the degree of damage to the test plants is rated in % damage in comparison to the untreated control.

The figures denote:

0%=no action

100%=total destruction.

In this test, for example the compounds obtained by preparation examples 1, 2 and 3 are well tolerated by crops, such as, for example, barley (15–20%), and exhibit strong activity against weeds such as, for example, amborosia (70–95%), chenopodium (70–90%), polygonom (99–100%) and viola (90–95%).

We claim:

1. A azolylsulphonylphenyluracil compound of formula I

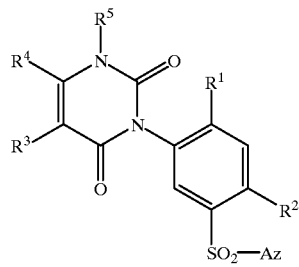

(I)

in which

Az represents pyrazolyl, imidazolyl or triazolyl, each of which is optionally mono- to trisubstitued by identical or different substituents from the group consisting of halogen, cyano, nitro, amino, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy or halogeno-$C_1$–$C_4$-alkylthio, $R^1$ represents hydrogen, cyano or halogen, $R^2$ represents cyano, nitro, halogen or a respectively optionally halogen substituted radical of the group consisting of $C_1$–$C_4$-alkyl and $C_1$–$C_4$-alkoxy, $R^3$ represents hydrogen, halogen, $C_1$–$C_4$-alkyl or $C_1$–$C_4$-halogenoalkyl, and $R^4$ represents hydrogen, $C_1$–$C_4$-alkyl or $C_1$–$C_4$-halogenoalkyl, and $R^5$ represents hydrogen, amino, formyl or a respectively optionally cyano-, halogen, or $C_1$–$C_2$-alkoxy-substituted radical from the group consisting of $C_1$–$C_4$-alkyl, $C_1$–$C_4$-alkenyl or $C_1$–$C_4$-alkinyl.

2. An azolylsulphonylphenyluracil of compound formula (I) according to claim 9, wherein Az represents pyrazolyl, imidazolyl or triazolyl, each of which is optionally mono- to trisubstitued by identical or different substituents from the group consisting of halogen, cyano, nitro, amino, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy or halogeno-$C_1$–$C_4$-alkylthio, $R^1$ represents hydrogen, cyano, fluorine or chlorine, $R^2$ represents cyano, nitro, fluorine, chlorine, bromine or a respectively optionally fluorine- and/or chlorine-substituted radical from the group consisting of $C_1$–$C_4$-alkyl and $C_1$–$C_4$-alkoxy, $R^3$ represents hydrogen, fluorine, chlorine, bromine or optionally fluorine- and/or chlorine-substituted $C_1$–$C_4$-alkyl, $R^4$ represents hydrogen or optionally fluorine- and/or chlorine-substituted $C_1$–$C_4$-alkyl, and $R^5$ represents hydrogen, amino, formyl or a respectively optionally cyano-, fluorine- and/or chlorine-, methoxy- or ethoxy-substituted radical from the group consisting of $C_1$–$C_4$-alkyl, $C_1$–$C_4$-alkenyl and $C_1$–$C_4$-alkinyl.

3. An azolylsulphonylphenyluracil of compound formula (I) according to claim 1, wherein Az represents pyrazolyl or imidazolyl, each of which is optionally mono-, di- or trisubstituted by identical or different substituents from the group consisting of chlorine, bromine, methyl, ethyl or trifluoromethyl, $R^1$ represents hydrogen, fluorine or chlorine, $R^2$ represents cyano or chlorine, $R^3$ represents hydrogen, fluorine, chlorine, bromine or respectively optionally fluorine- and/or chlorine-substituted methyl or ethyl, $R^4$ represents respectively optionally fluorine- and/or chlorine-substituted methyl or ethyl, and $R^5$ represents hydrogen, amino or respectively optionally fluorine- and/or chlorine-substituted methyl, ethyl, n- or i-propyl, propenyl or propinyl.

4. Herbicidal compositions comprising one or more azolylsulphonylphenyluracil compound of formula (I) according to claim 1 and an inert carrier.

5. Method of controlling undesired plants comprising allowing an effective amount of one or more azolylsulphonylphenyluracil compound of formula (I) according to claim 1 to act on undesired plants and/or their habitat.

6. Herbicidal compositions comprising one or more azolylsulphonylphenyluracil compound of formula (I) according to claim 1 in combination with extenders and/or surface-active agents.

* * * * *

UNITED STATES PATENT AND TRADEMARK OFFICE
CERTIFICATE OF CORRECTION

PATENT NO. : 6,074,989  
DATED : June 13, 2000  
INVENTOR(S) : Andree et al.

Page 1 of 1

It is certified that error appears in the above-identified patent and that said Letters Patent is hereby corrected as shown below:

<u>Title page,</u>
PCT Pub. Date, delete "May 17, 1997" and substitute -- May 17, 1996 --

Signed and Sealed this

Twenty-sixth Day of February, 2002

Attest:

JAMES E. ROGAN  
*Attesting Officer*     *Director of the United States Patent and Trademark Office*